US008257357B2

(12) United States Patent
Hatch

(10) Patent No.: US 8,257,357 B2
(45) Date of Patent: Sep. 4, 2012

(54) COMBINATION OF A MOTOR DRIVEN OSCILLATING ORTHOPEDIC RESHAPING AND RESURFACING TOOL AND A SURFACE-MATCHING SHEET METAL PROSTHESIS

(76) Inventor: Edwin Burton Hatch, The Villages, FL (US)

( * ) Notice: Subject to any disclaimer, the term of this patent is extended or adjusted under 35 U.S.C. 154(b) by 388 days.

(21) Appl. No.: 12/383,202

(22) Filed: Mar. 21, 2009

(65) Prior Publication Data
US 2010/0076439 A1   Mar. 25, 2010

Related U.S. Application Data

(60) Provisional application No. 61/192,848, filed on Sep. 23, 2008.

(51) Int. Cl.
*A61B 17/00* (2006.01)
(52) U.S. Cl. .......................................... 606/79
(58) Field of Classification Search ............. 606/79–85, 606/86, 86 R, 87–91; 451/121, 163; 433/51, 433/102, 118–125, 142, 166
See application file for complete search history.

(56) References Cited

U.S. PATENT DOCUMENTS

| | | | | |
|---|---|---|---|---|
| 3,964,212 A * | 6/1976 | Karden | ......................... | 451/358 |
| 4,176,453 A * | 12/1979 | Abbott | ............................ | 433/82 |
| 5,462,548 A * | 10/1995 | Pappas et al. | .................. | 606/80 |
| 5,531,596 A * | 7/1996 | Melde | ............................ | 433/104 |
| 5,582,618 A * | 12/1996 | Chin et al. | ..................... | 606/170 |
| 6,062,960 A * | 5/2000 | Kai et al. | ....................... | 451/357 |
| 6,110,176 A * | 8/2000 | Shapira | .......................... | 606/80 |
| 6,306,024 B1 * | 10/2001 | Kai et al. | ....................... | 451/357 |
| 6,758,731 B2 * | 7/2004 | Dutterer et al. | ............... | 451/357 |
| 6,796,889 B2 * | 9/2004 | Marton | ......................... | 451/357 |
| 6,846,314 B2 * | 1/2005 | Shapira | .......................... | 606/80 |
| 6,875,095 B2 * | 4/2005 | Walker | ......................... | 451/357 |
| 6,875,217 B2 * | 4/2005 | Wolford | ......................... | 606/81 |
| 7,189,154 B1 * | 3/2007 | Karppinen et al. | ........... | 451/449 |
| 7,300,337 B1 * | 11/2007 | Sun et al. | ....................... | 451/295 |
| 7,364,499 B1 * | 4/2008 | Karppinen et al. | ........... | 451/449 |
| RE40,354 E * | 6/2008 | Cornell et al. | ................ | 361/648 |
| 2004/0010258 A1 * | 1/2004 | Carusillo et al. | ................ | 606/79 |
| 2004/0243134 A1 * | 12/2004 | Walker et al. | .................... | 606/79 |
| 2005/0171604 A1 * | 8/2005 | Michalow | .................. | 623/14.12 |
| 2005/0192673 A1 * | 9/2005 | Saltzman et al. | .......... | 623/21.18 |
| 2005/0203342 A1 * | 9/2005 | Kucklick et al. | .............. | 600/156 |
| 2006/0100632 A1 * | 5/2006 | Fell | ................................. | 606/81 |
| 2006/0246823 A1 * | 11/2006 | Morita et al. | ..................... | 451/7 |
| 2009/0018560 A1 * | 1/2009 | Mayer et al. | .................. | 606/151 |

* cited by examiner

*Primary Examiner* — Thomas Barrett
*Assistant Examiner* — Diana S Jones

(57) ABSTRACT

The combination of a motor driven oscillating orthopedic reshaping and resurfacing tool and multiple surface-matching sheet metal prostheses minimally resurface bones of the knee and other joints. Said resurfacing tool incorporates multiple interchangeable cutting heads, each configured to conform to the anatomical surface of a different bone end of the knee joint or other joint, and incorporates a replaceable elastomeric cover having an annular containment cup with an incoming sterile-liquid tube and an out-going waste-liquid tube to flush debris from the surgical site. Each said prostheses, stamped from orthopedic metal sheet and having at least one mounting attachment, is configured to conform to the anatomical surface of a different bone end of the knee joint, or other joint, after said tool has resurfaced that bone end. When implanted onto said bone end, a prefect fit is achieved.

6 Claims, 6 Drawing Sheets

SECTION A-A

COMBINATION OF A MOTOR DRIVEN OSCILLATING ORTHOPEDIC RESHAPING AND RESURFACING TOOL AND A SURFACE-MATCHING SHEET METAL PROSTHESIS

CROSS-REFERENCE TO RELATED APPLICATIONS

This Application claim priority to Provisional Application Ser. No. 61/192,848, filed on Sep. 23, 2008.

RELATED U.S. PATENT DOCUMENTS

| | | |
|---|---|---|
| 3,964,212 | Jun. 22, 1976 | Karl Gosta Karden |
| 4,176,453 | Dec. 4, 1979 | Sheldon J. Abbott |
| 5,531,596 | Jul. 2, 1996 | Chris R. Melde |
| 6,062,960 | May 16, 2000 | Nobuto Kai, et. al. |
| 6,110,176 | Aug. 29, 2000 | Ira L. Shapira |
| 6,306,024 | Oct. 23, 2001 | Nobuto Kai, et. al. |
| 6,758,731 | Jul. 6, 2004 | David Eric Dutterer, et.al. |
| 6,796,889 | Sep. 28, 2004 | Miksa Marton |
| 6,846,314 | Jan. 25, 2005 | Ira L. Shapira |
| 6,875,095 | Apr. 5, 2005 | Andrew Walker |
| 20050171604 | Aug. 4, 2005 | Alexander Michalow |
| 20050192673 | Sep. 1, 2005 | Charles L Saltzman, et. al. |
| 7,189,154 | Mar. 13, 2007 | Rodney J. Karpinnen et.al. |
| 7,300,337 | Nov. 27, 2007 | Yung-yung Sun, et.al. |
| 7,364,499 | Apr. 29, 2008 | Rodney J. Karpinnen et.al. |
| 20090018560 | Jan. 15, 2009 | Jorg Mayer, et. al. |

U.S. PATENT APPLICATION PUBLICATIONS

| | | |
|---|---|---|
| 2004/0243134 A1 | Dec. 2, 2004 | Walker, Peter Stanley, et.al. |
| 2006/0246823 | Nov. 2, 2006 | Hiroshi, Morita, et. al. |
| 2006/0100632 | May 11, 2006 | Fell, Barry M. |
| RE40,354 | May 27, 2008 | Colin, Duffy |

FEDERALLY SPONSORED RESEARCH OR DEVELOPMENT

[Not Applicable]

PARTIES TO A JOINT RESEARCH AGREEMENT

[Not Applicable]

INCORPORATION-BY-REFERENCE OF MATERIAL SUBMITTED ON A COMPACT DISC

[Not Applicable]

BACKGROUND OF THE INVENTION

1. Field of the Invention

This invention relates generally to the minimally invasive orthopedic surgical repair or reconstruction of the knee and other joints.

2. Description of Related Art

In current orthopedic surgical repair or reconstruction of the knee and other joints, large amounts of bone are normally removed from bone ends in preparation for implanting prostheses. These prosthetic components can be massive and resection of the bone ends generally leaves little remaining bone for later surgical procedures required because of an accident or deteriorating bone conditions. The patient's surgical results vary widely with the skill of the surgeon, the type of prosthetic components implanted, and the type of surgical equipment available. Recovery may be more difficult if the patient must adjust to changed bone alignments and tendon tensions during the healing process. The cost of orthopedic joint surgery may be prohibitive for poor patients in third world countries.

BRIEF SUMMARY OF THE INVENTION

The combination of a motor driven oscillating orthopedic reshaping and resurfacing tool and surface-matching sheet metal prostheses as taught here is designed to resurface bone ends in the minimally invasive orthopedic surgical repair or reconstruction of the knee joint and other anatomical joints. After a bone end has been reshaped and resurfaced by the oscillating orthopedic reshaping and resurfacing tool, a surface-matching sheet metal prosthesis, configured so as to conform to the surface configuration of that same bone end after it has been resurfaced, is implanted onto that bone end. Because the cutting surface of the cutting head and the surface of the corresponding prosthesis have an identical configuration, more consistently perfect joint surgeries can be achieved. Recovery can be faster and less painful. The patient retains the original joint configuration and ligament relationships. Surgery using this tool and prosthesis combination retains the majority of the bone of the bone end permitting a total joint replacement surgery should that be required because of an accident or deteriorating bone conditions. Surgeons can achieve improved surgical results with reduced time in surgery allowing hospitals and surgeons to serve more patients. Tools and prosthetics cost less and less and surgeons in third world countries can perform successful low cost orthopedic joint surgeries.

BRIEF DESCRIPTION OF THE SEVERAL VIEWS OF THE DRAWINGS

FIG. 1 shows an oscillating orthopedic reshaping and resurfacing tool [16] having a motor [1] which rotates a motor shaft [2] which has an end [3] eccentric to the longitudinal axis of the motor shaft [2] with a bearing [4] mounted there on. A removable and replaceable cutting head [5] is mounted onto that bearing [4] and has a cutting surface [6]. The cutting head [5] is flexibly located and retained by a removable and replaceable elastomeric cover [9]. When driven by the motor [1], the bearing [4] mounted onto the end [3] eccentric to the longitudinal axis of the motor shaft [2] of the motor shaft [2] oscillates the cutting head [5] which when pressed against the bone end [8] will reshape and resurface that bone end [8] to fit a surface-matching sheet metal prosthesis [10]. The elastomeric cover [9] is fitted against and is located by the motor housing [15] and is designed to seal against the removable and replaceable cutting head [5] and against the bone end [8]. This oscillating orthopedic reshaping and resurfacing tool [16] also has a hand grip [13], a power conduit [14], and an on/off control [25].

FIG. 2 shows an oscillating orthopedic reshaping and resurfacing tool [18] having a motor [1], mounted within a cylindrical motor housing [15], which rotates a motor shaft [2] which has an end [3] eccentric to the longitudinal axis of the motor shaft [2] with a bearing [4] mounted there on. A removable and replaceable cutting head [5] is mounted onto the bearing [4] and has a cutting surface [6]. The cutting head [5] is flexibly located and retained by a removable and replaceable elastomeric cover [17]. When driven by the motor [1], the bearing [4] mounted onto the end [3] eccentric to the longitudinal axis of the motor shaft of the motor shaft [2] oscillates the cutting head [5] which when pressed against the bone end [8] will reshape and resurface that bone end [8] to fit a surface-matching sheet metal prosthesis [10]. The elastomeric cover [17] is fitted against and is located by the motor housing [15]. This removable elastomeric cover [17] incorporates an annular containment cup [7] which is designed to seal against the cutting head [5] and against the bone end [8] so as to contain the debris during the reshaping and resurfacing process. The containment cup [7] also incorporates an in-coming sterile water tube [11] and an out-going waste water tube [12] to flush and remove debris from the bone end during the resurfacing process. This oscillating orthopedic reshaping and resurfacing tool [18] also has a hand grip [13], a power conduit [14], and an on/off control [25].

FIG. 3 shows an oscillating orthopedic reshaping and resurfacing tool [27] having a motor [1], mounted within a cylindrical motor housing [15], which rotates a shaft [2] which has an end [3] eccentric to the longitudinal axis of the motor shaft with a bearing [4] mounted there on. A removable and replaceable cutting head [5] is mounted onto the bearing [4] and has a cutting surface [6]. The cutting head [5] is flexibly located and retained by a removable and replaceable elastomeric cover [9] and by a spring [21]. When driven by the motor [1] the bearing [4] mounted onto the end [3] eccentric to the longitudinal axis of the motor shaft of the motor shaft [2] oscillates the cutting head [5] which when pressed against the bone end [8] will reshape and resurface the bone end [8] to fit a surface-matching sheet metal prosthesis [10]. The elastomeric cover [9], which is designed to seal against the removable and replaceable cutting head [5] and against the bone end [8], is fitted against and is located by the motor housing [15]. The oscillating orthopedic reshaping and resurfacing tool [27] also has a hand grip [13], a power conduit [14], and an on/off control [25].

FIG. 4 shows an oscillating orthopedic reshaping and resurfacing tool [28] having a motor [1], mounted within a cylindrical motor housing [15], which rotates a shaft [2] which has an end [3] eccentric to the longitudinal axis of the shaft with a bearing [4] mounted there on. A removable and replaceable cutting head [5] is mounted onto the bearing [4] and has a cutting surface [6]. The cutting head [5] is flexibly located and retained by a removable and replaceable elastomeric cover [9] and by elastomeric tubes [22]. When driven by the motor [1] the bearing [4] mounted onto the end [3] eccentric to the longitudinal axis of the motor shaft [2] oscillates the cutting head [5] which when pressed against the bone end [8] will reshape and resurface the bone end [8] to fit a surface-matching sheet metal prosthesis [10]. The elastomeric cover [9], which is designed to seal against the removable and replaceable cutting head [5] and against the bone end [8], is fitted against and is located by the motor housing [15]. The oscillating orthopedic reshaping and resurfacing tool [28] also has a hand grip [13], a power conduit [14], and an on/off control [25].

FIG. 5 shows a removable and replaceable cutting head [5], with abrasive particles [23] on the upper cutting surface, and a bearing [4].

FIG. 6 shows a removable and replaceable cutting head [5], with multiple sharp metal teeth [25] on the upper cutting surface, and a bearing [4].

FIG. 7 shows a removable and replaceable cutting head [24] with abrasive particles [23] on the upper cutting surface of a removable upper cover [19], and a bearing [4].

FIG. 8 shows a removable and replaceable cutting head [24] with multiple sharp metal teeth [25] on a removable upper cover [19,] and a bearing [4].

FIG. 9 shows a side sectional view and a bottom sectional view of the removable and replaceable cutting head [5] and elastomeric cover [9] of FIG. 1 showing the elastomeric cover [9] having anti-rotational locking tabs [26] to further prevent the cutting head [5] from rotating.

DETAILED DESCRIPTION OF THE INVENTION

Figure 1:
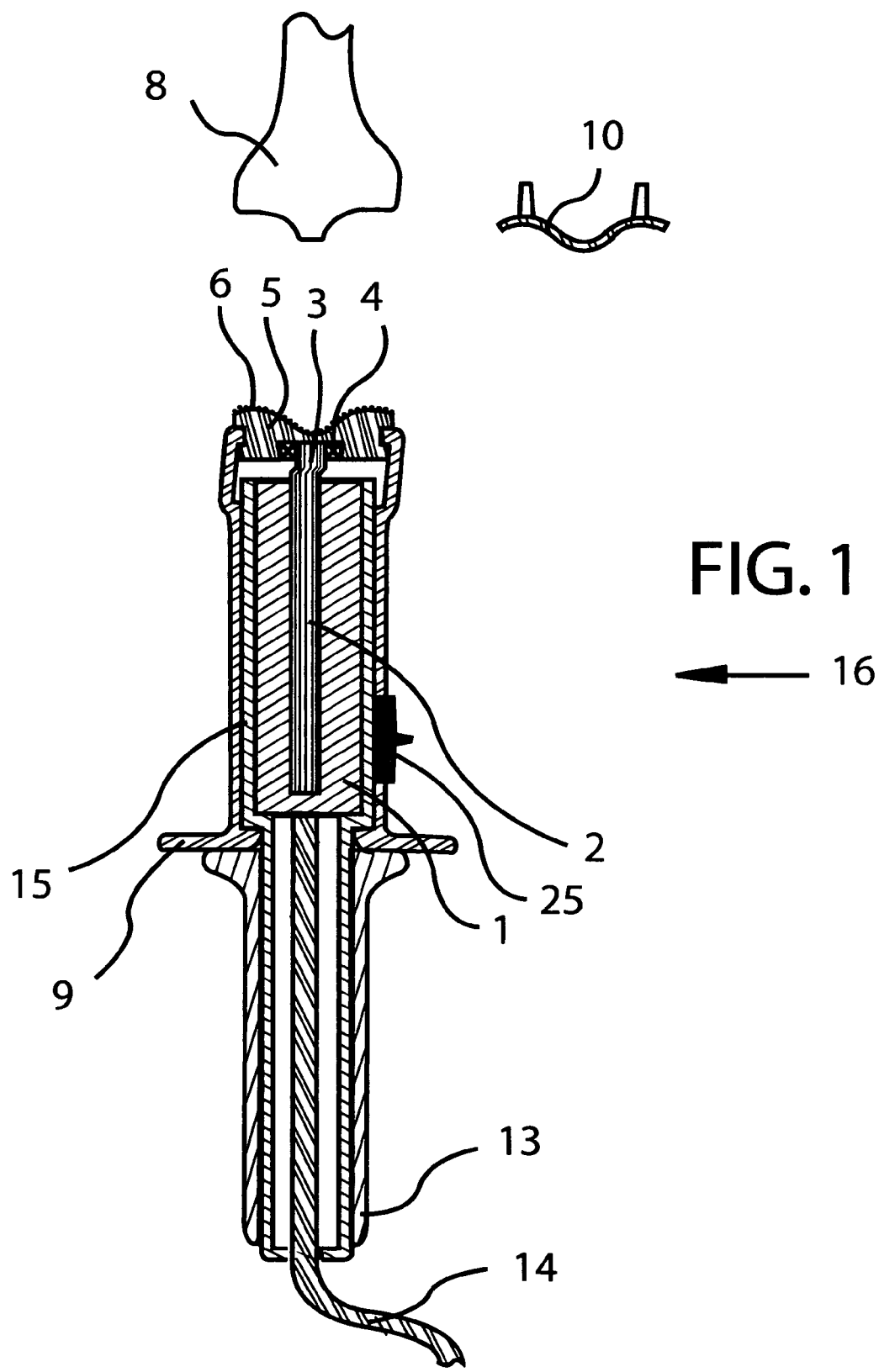
FIGS. 1-4 and 9 [Original]
Figure 2:
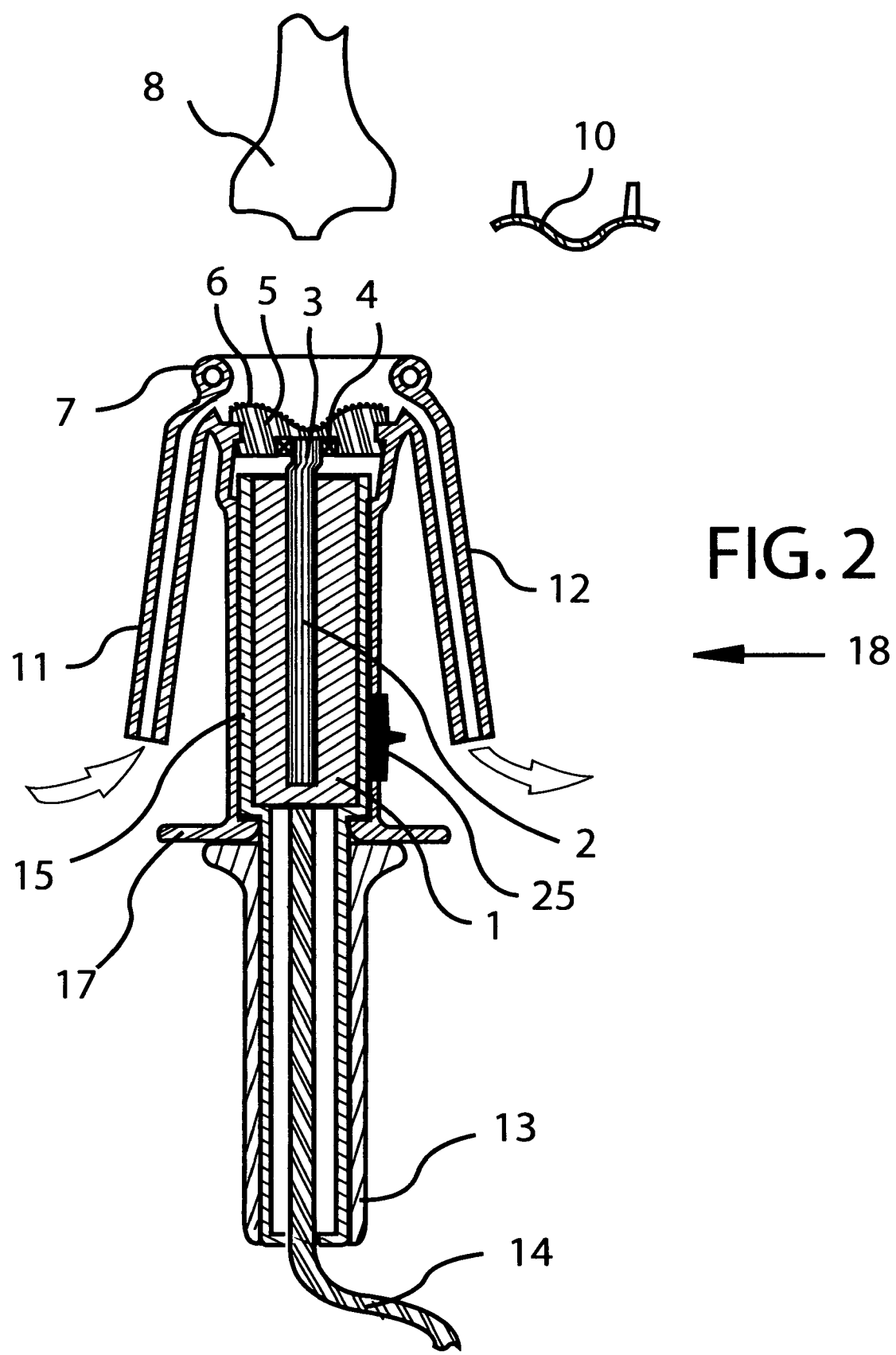
Figure 3:
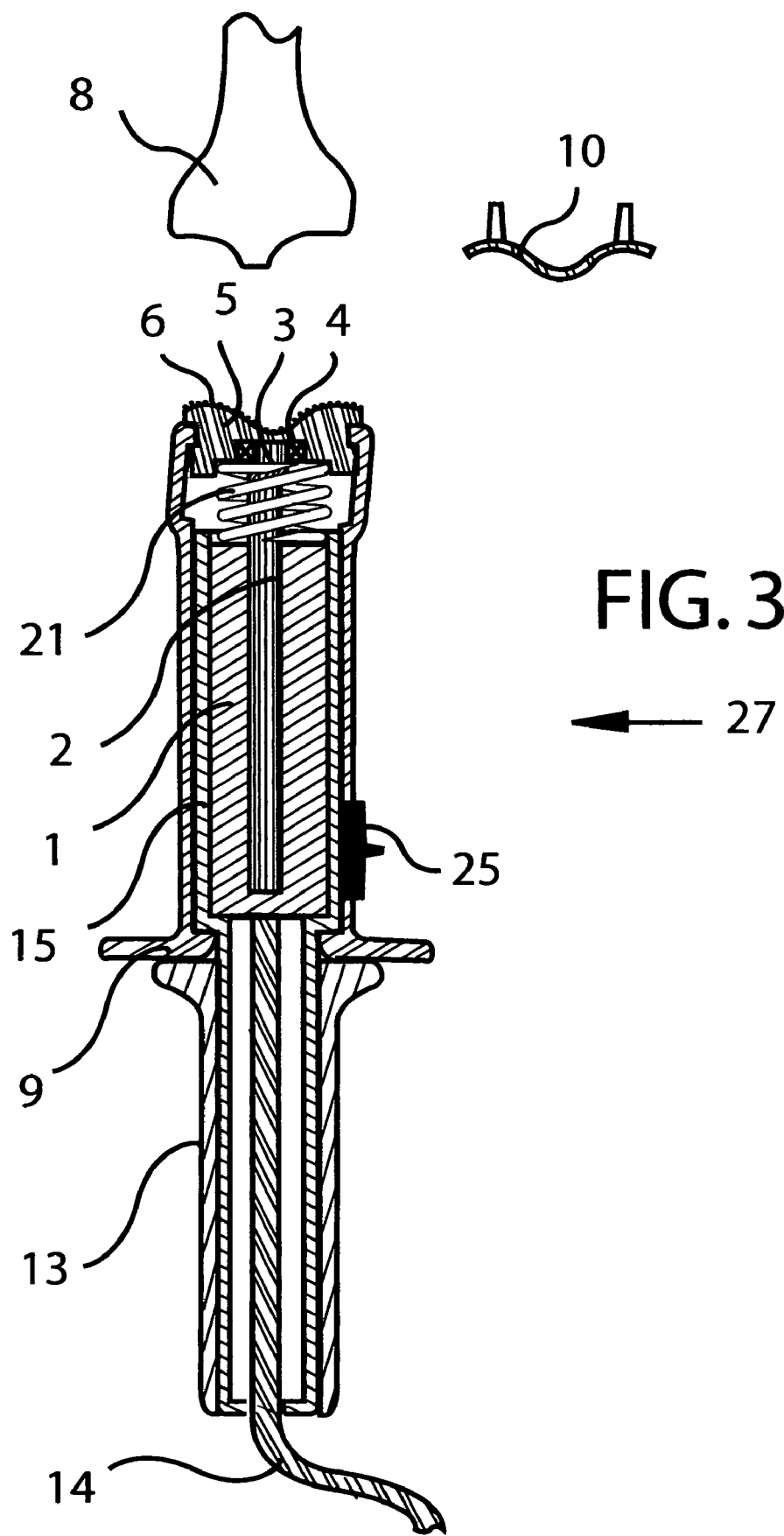
Figure 4:
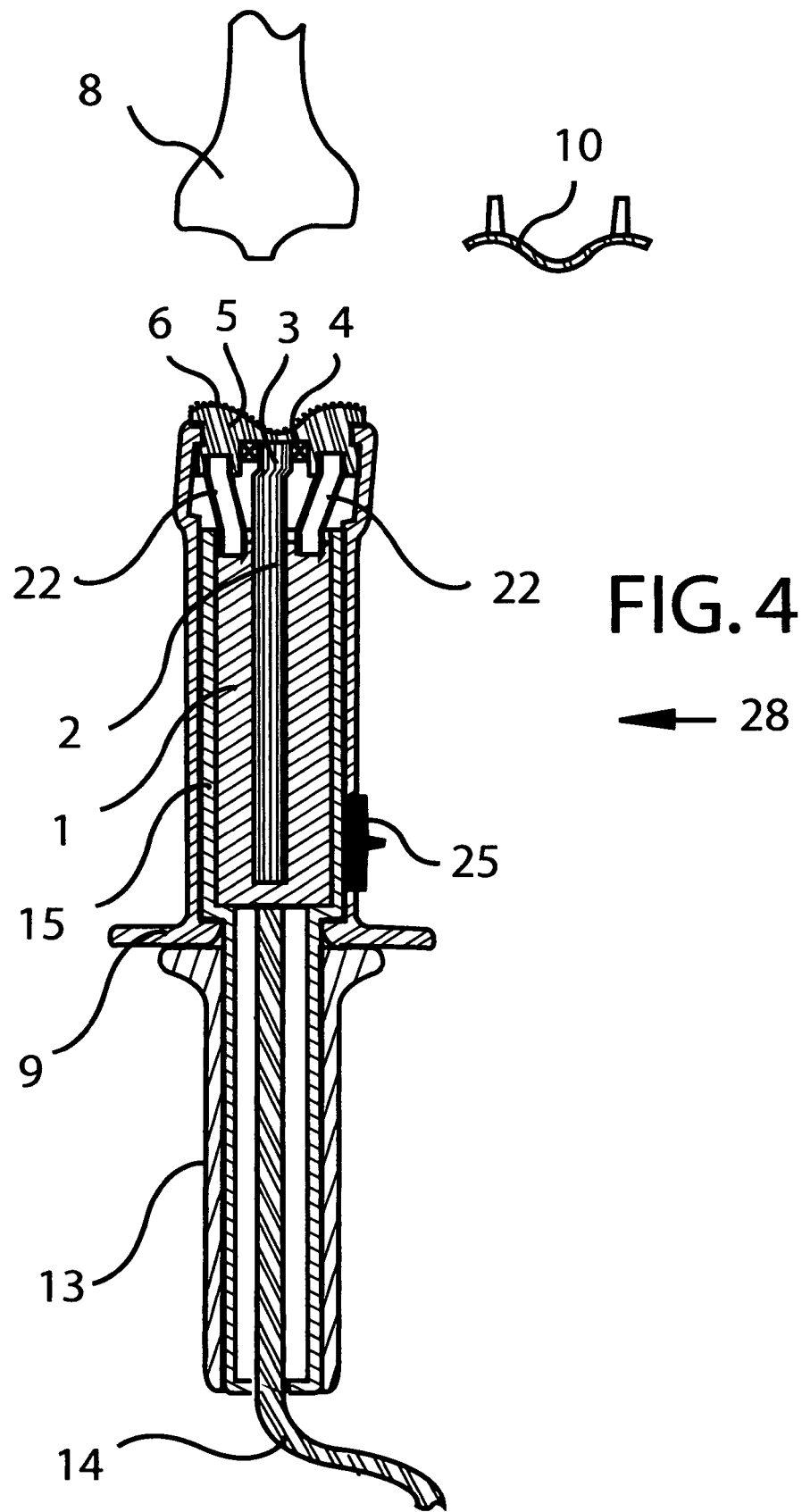
Figure 5:
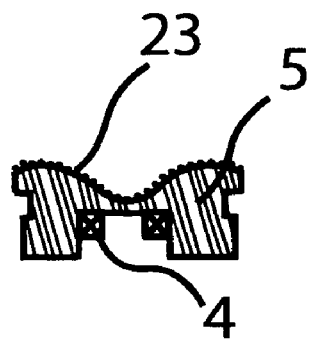
FIGS. 5-8 Modified].
Figure 6:
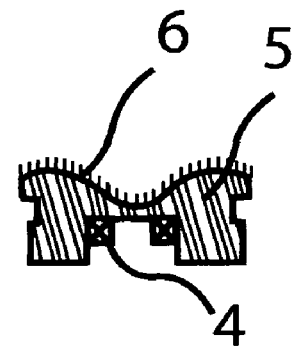
Figure 7:
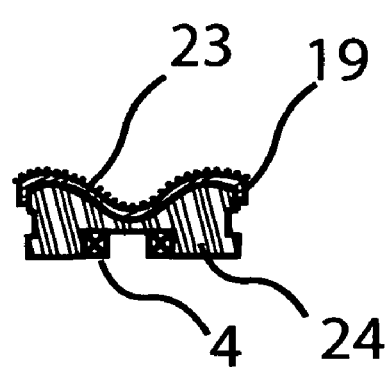
Figure 8:
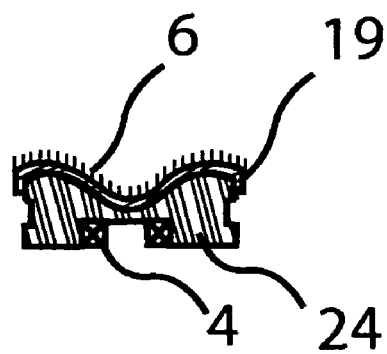
Figure 9:
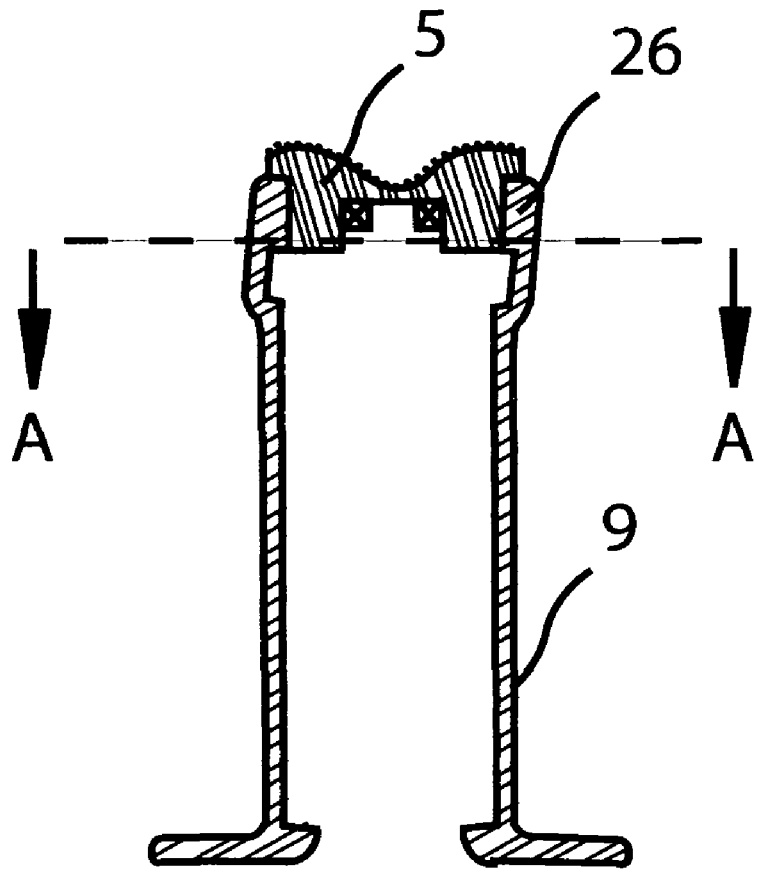
Figure 9:
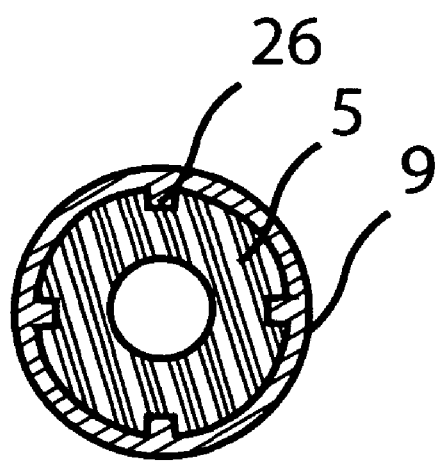

The combination of a motor driven oscillating orthopedic reshaping and resurfacing tool and a surface-matching minimally-thick prosthesis, here in taught, is designed for the minimally invasive resurfacing of bone ends in the orthopedic surgical repair or reconstruction of the knee joint, and other anatomical joints. The motor driven oscillating orthopedic reshaping and resurfacing tool incorporates a number of interchangeable and replaceable cutting heads, each having it's cutting surface coated with abrasive particles and configured so as to conform to the surface configuration of the end of a different bone of the knee joint or of another anatomical joint, and further incorporates a removable and replaceable elastomeric cover, having an annular containment cup with an incoming sterile-liquid tube and an outgoing waste-liquid tube whereby cutting debris can be flushed and removed from the surgical site. This elastomeric cover also flexibly mounts, retains, and seals the interchangeable and replaceable cutting head to the tool and to the bone end to be resurfaced. A number of surface-matching sheet metal prostheses are provided in this combination, each being stamped form orthopedic sheet metal and configured so as to conform to the surface configuration of the end of a different bone of the knee joint or of another anatomical joint after that bone end has been resurfaced by the motor driven oscillating orthopedic reshaping and resurfacing tool utilizing the cutter head configured to conform to the full complex anatomical surface configuration of the end of that bone, each surface-matching sheet metal prosthesis having at least one locating attachment on which it can be implanted onto a resurfaced bone end.

What is claimed is:

1. A combination of an oscillating orthopedic reshaping and resurfacing tool and a surface-matching sheet metal prosthesis, designed to reshape and resurface bone ends in the orthopedic surgical repair; said oscillating orthopedic reshaping and resurfacing tool comprising:

a motor housing containing a motor having a rotatable motor shaft with an end eccentric to the longitudinal axis of said motor shaft;

a bearing mounted onto said eccentric end;

a removable and replaceable cutting head, wherein said cutting head is one of many removable and replaceable cutting heads, each having a cutting surface comprised of abrasive particles, wherein said cutting heads are mounted onto said bearing;

a removable and replaceable elastomeric cover, incorporating an annular containment cup which flexibly mounts and retains said cutting head to said motor housing and seals said cutting head against said motor housing and against said bone end to be resurfaced, said cup further incorporating an incoming sterile-liquid tube and an out going waste-liquid tube whereby cutting debris may be flushed and removed during the surgical reshaping and resurfacing of the bone end;

a hand grip;
a power conduit;
an on/off control; and
wherein said combination further comprises a surface-matching sheet metal prosthesis, stamped from orthopedic sheet metal, wherein said prosthesis is one of many surface-matching sheet metal prostheses, configured to be attached to the surface configuration of the bone end, after said cutting surface of said cutting head has resurfaced said bone end, said prosthesis further comprises at least one locating attachment on which it can be mounted to said resurfaced bone end.

2. The combination of said oscillating orthopedic reshaping and resurfacing tool and said surface-matching sheet metal prostheses of claim 1 where in said cutting surface of said cutting head is configured so as to conform to the surface configuration of the surfaces of the tibial plateau of the tibia and wherein said prosthesis is configured so as to conform to surface configuration of the tibial plateau of the tibia after said cutting head has resurfaced said tibial plateau.

3. The combination as set forth in claim 1 where in said removable and replaceable elastomeric cover further incorporates anti-rotational locking tabs to prevent said cutting head from rotating during the reshaping and resurfacing of said bone end.

4. An oscillating orthopedic reshaping and resurfacing tool comprising:
a motor housing containing a motor having a rotatable motor shaft with an end eccentric to the longitudinal axis of said motor shaft;
a bearing mounted onto said eccentric end;
multiple removable and replaceable cutting heads, wherein said cutting heads each have a cutting surface comprised of abrasive particles, wherein said cutting heads can be mounted onto said bearing;
a removable and replaceable elastomeric cover, incorporating an annular containment cup which flexibly mounts and retains said cutting head to said motor housing and seals said cutting head against said motor housing and against said bone end to be resurfaced, said cup further incorporating an incoming sterile-liquid tube and an out going waste-liquid tube whereby cutting debris may be flushed and removed, during the surgical reshaping and resurfacing of the bone end;
a hand grip;
a power conduit; and
an on/off control.

5. The cutting head of claim 4 where in said cutting surface is configured so as to conform to the surface configuration of the surfaces of the tibial plateau of the tibia.

6. The combination as set forth in claim 4 where in said removable and replaceable elastomeric cover further incorporates anti-rotational locking tabs to prevent said cutting head from rotating during the reshaping and resurfacing of said bone end.

* * * * *